United States Patent

Tuba et al.

[11] 4,200,636
[45] Apr. 29, 1980

[54] 3-AMINO-17A-AZA-D-HOMOANDROSTANE COMPOUNDS, AND PHARMACEUTICAL COMPOSITIONS CONTAINING THEM

[75] Inventors: Zoltán Tuba; Mária Mársai; Sandor Görög; Kátalin Biró; Egon Kárpáti; Laszlo Szporny, all of Budapest, Hungary

[73] Assignee: Richter Gedeon Vegyeszeti Gyar Rt., Budapest, Hungary

[21] Appl. No.: 934,799

[22] Filed: Aug. 17, 1978

[30] Foreign Application Priority Data

Aug. 18, 1977 [HU] Hungary .................. RI 644

[51] Int. Cl.² ............... C07D 401/04; A61K 31/495; C07D 401/10; A61K 31/47
[52] U.S. Cl. .................. 424/250; 544/361; 546/77; 424/258
[58] Field of Search ..... 260/286 Q, 288 CF, 289 AZ; 544/361; 424/250, 258; 546/77

[56] References Cited

PUBLICATIONS

Gandiha, A. et al., J. Pharm. Pharmacol., 1974, vol. 26, pp. 871–877.
Morrison, R. and R. Boyd, "Organic Chemistry," 3rd ed., Allyn and Bacon, Inc. Boston, 1976, p. 520.
Muller, Eugen, "Methoden der Organischen Chemie", Houben-Wail-Bond X1/1-Stickstoffverbindungen II Amine, (1957), p. 243.
Sidgwick, N. "The Organic Chemistry of Nitrogen", Clarendon Press, Oxford, (1966), p. 250.

Primary Examiner—Alton D. Rollins
Assistant Examiner—Lisa Jones
Attorney, Agent, or Firm—Karl F. Ross

[57] ABSTRACT

The invention relates to new 3-amino-17a-aza-D-homo-5α-androstane derivatives of the general formula I

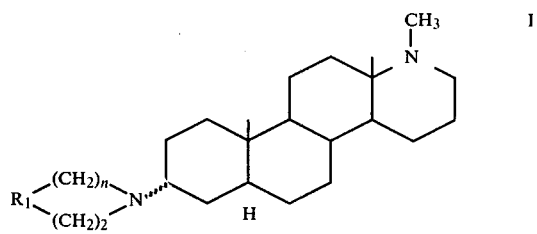

wherein $R_1$ represents a methylene or an $>N-CH_3$ group, and n stands for 1 or 2, and the acid addition salts and the quaternary salts of the general formula

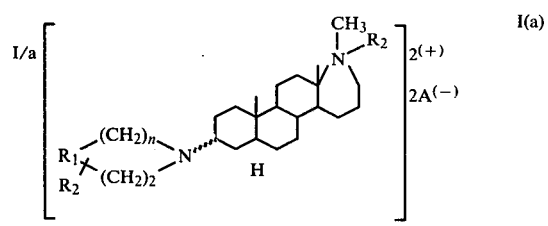

thereof, wherein $R_2$ stands for an alkyl or alkenyl group having from 1 to 4 carbon atoms, and A represents a halogen atom, provided that if $R_1$ stands for an $>N-CH_3$ group, $R_2$ is attached to the nitrogen of that $>N-CH_3$ group. The new compound possess a non-polarizing neuromuscular blocking activity and have a short activity period.

7 Claims, No Drawings

3-AMINO-17A-AZA-D-HOMOANDROSTANE COMPOUNDS, AND PHARMACEUTICAL COMPOSITIONS CONTAINING THEM

This invention relates to new 3-amino-17a-aza-D-homoandrostane derivatives, their preparation and pharmaceutical preparations containing them. More particularly the invention relates to 3-amino-17a-aza-D-homoandrostane derivatives of the formula

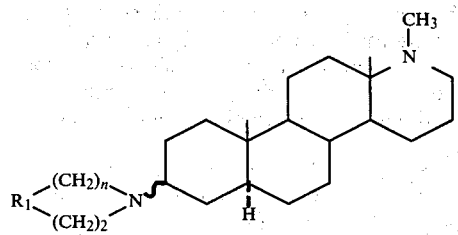

wherein $R_1$ is a methylene or an $>N-CH_3$ group;
$n = 1$ or 2; and
the symbol ∿ represents an α- or β-configuration, and acid-addition salts and quaternary salts thereof. The quaternary salts of the compounds having the general formula I are encompassed by the formula I(a)

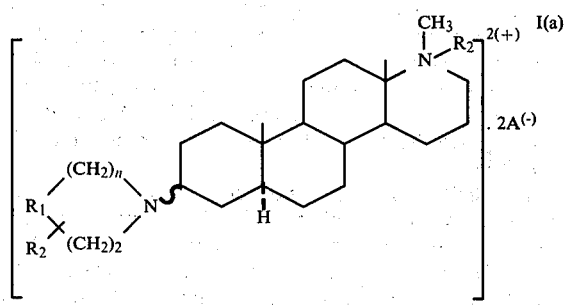

wherein $R_1$, n and the symbol ∿ have the same meanings as given above, and
$R_2$ is a $C_1$ to $C_4$ alkyl or $C_1$ to $C_4$ alkenyl group, provided that where $R_1$ is an $>N-CH_3$ group, $R_2$ is attached to the $>N-CH_3$ group;
A represents a halogen atom.

Compounds of the formulae I and I(a) and the intermediates of their synthesis characterized by the formulae

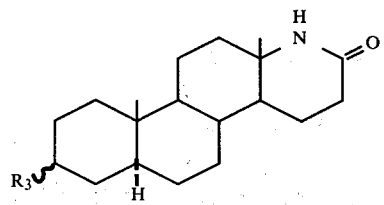

wherein $R_3$ is an alkane-sulphonyloxy, an aryl- or an aralkyl-sulphonyloxy group;

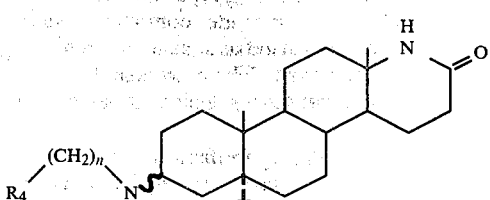

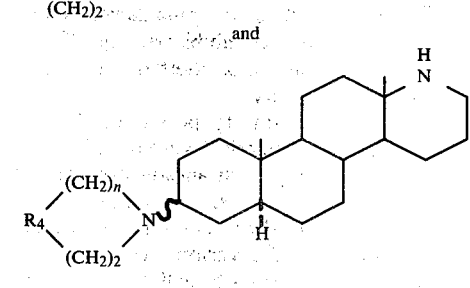

are new compounds which have not been reported in the literature. The structurally closest known compounds are described in the British Pat. No. 1,345,971. These compounds are 17-aza-pregnane derivatives and show bacterid and cholesterine level decreasing activity. The compound of the formula

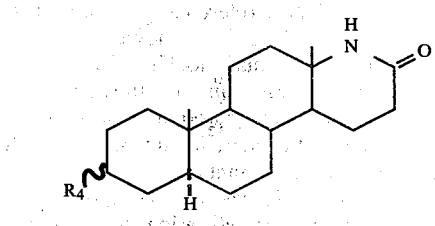

wherein $R_4$ is an α- or β-hydroxyl group, used as a starting material is well known and has for instance been described in Tetrahedron 21 (4), 734–57 (1965); Helv. Chim. Acta 38, 1404 (1955).

The new compounds of the formula I possess valuable physiological properties and their quaternary salts of the formula I(a) are excellent non-depolarizing neuromuscular blocking agents having a short activity period.

Especially preferred compounds according to the invention include the following compounds of formula I(a):
3α-Pyrrolidino-17a-methyl-17a-aza-D-homo-5α-androstane dimethoiodide;
3β-Pyrrolidino-17a-methyl-17a-aza-D-homo-5α-androstane dimethoiodide and
3β-Pyrrolidino-17a-methyl-17a-aza-D-homo-5α-androstane dimethobromide;
and the most preferred compound is
3α-Pyrrolidino-17a-methyl-17a-aza-D-homo-5α-androstane dimethobromide.

It is well known that in therapy those muscle relaxants are used which have a more favorable effect—i.e. are easy to control—and which are of non-polarizing—i.e. competitive—type [Negwer (1971) 4821], such as pancuronium bromide. These compounds generally have a prolonged activity and as a short activity-type muscle relaxant almost exclusively the depolarizing suxamethonium is employed [Negwer (1971) 2289].

Until now there has been no muscle relaxant preparation in the therapy which has a short activity period and which is of the non-depolarizing type. The object of the present invention is to provide compounds having about the same activity period as suxamethonium but of to the non-polarizing type. The new compounds are therefore easy to control during their therapeutic application.

The compounds according to the invention are competitive neuromuscular blocking agents, i.e. inhibit the transmission of the nervous stimulus to the transverse muscles. The activity of these compounds can be terminated by acetylcolinesterase inhibitors, e.g. fizostigmine. They have no influence on the blood circulation and on the endocrine activity.

The potency and the activity period of the compounds according to the invention were tested on anesthesized cats and alert dogs. On anesthesized cats the peroneal nerve was electrically stimulated and the corresponding contractions of the tibialis muscle was registrated. The i.v. doses of the various test compounds which reduced the contractions to half of their original values were determined ($ED_{50}$-values). In the attached Table I the $ED_{50}$-values and the corresponding activity periods are shown, the term "activity period" is intended to mean the time interval between the first appearance of the effect of the test compounds and the restoration of the normal muscle contractions. For each test compound 4 doses were used and for each dose 6 animals were examined. As a reference compound suxamethonium was used, which is a known compound widely used as a neuromuscular blocking agent having a short activity period. It was found that the compounds according to the invention caused a neuromuscular block which had about the same length of time as the block induced by suxamethonium.

To alert dogs (6 animals for each test compound) four doses causing a total muscle relaxation were administered and the time between the administration and the total muscle relaxation as well as the time between the administration and the disappearance of the activity was measured. The experimental data are set forth in the Table II. It has been found that the time of disappearance is shorter for the new compounds than for suxamethonium.

Table I

| Compound | $ED_{50}$ (mcg/kg) | Activity period(min) |
|---|---|---|
| 3 α-Pyrrolidino-17a-methyl-17a-aza-D-homo-5α-androstane-di-methobromide | 100 | 11.2 |
| 3 αPyrrolidino-17a-methyl-17a-aza-D-homo-5α-androstane-di-methoiodide | 120 | 12.4 |
| 3 β-Pyrrolidino-17a-methyl-17a-aza-D-homo-5α-androstane-di-methobromide | 125 | 13.0 |
| 3 β-Pyrrolidino-17a-methyl-17a-aza-D-homo-5α-androstane-di-methoiodid | 105 | 12.6 |
| Suxamethonium | 60 | 11.0 |

Table II

| Compound | Dose | Time until the max. effect(sec) | Activity period (min) |
|---|---|---|---|
| 3 α-Pyrrolidino-17a-methyl-17a-aza-D-homo-5- α-androstane-di-methobromide | 100 | 18 | 8.6 |
| 3 α-Pyrrolidino-17a-methyl-17a-aza-D-homo-5α-androstane-di-methoiodide | 100 | 19 | 8.5 |
| 3 β-Pyrrolidino-17a-methyl-17a-aza-D-homo-5 α-androstane-di-methobromide | 100 | 21 | 9.5 |
| 3 β-Pyrrolidino-17a-methyl-17a-aza-D-homo-5α-androstane-di-methoiodide | 100 | 17 | 8.8 |
| Suxamethonium | 100 | 16 | 10.3 |

The biologically active compounds according to the invention are used for pharmacological purposes in the form of conventional pharmaceutical compositions.

The compounds according to the invention may be formulated into pharmaceutical compositions in the conventional manner.

Thus according to a further feature of the present invention there are provided pharmaceutical compositions comprising at least one compound of formula I or I(a) or a physiologically compatible acid addition salt of a compound of formula I in association with a pharmaceutical carrier or excipient.

The pharmaceutical compositions according to the invention are suitable for parenteral administration.

As pharmaceutical carriers various inert compounds are used, which do not react with the active ingredients, e.g. water. The compositions can also be sterilized.

The compositions may also contain various additives which change the osmotic pressure, e.g. salts or buffers.

In order to prepare injectable solutions the active ingredients are dissolved in a pyrogen-free physiological sodium chloride solution or in water distilled twice to give formulations having an active ingredient concentration of 0.5 to 10 mg./ml. The injectable solutions are then sterilized and filled into ampules under sterile conditions.

For the treatment of adult human patients the active ingredients are administered in a dose of 0.1 to 0.5 mg./body weight. They are advantageously used to facilitate short medical treatments, such as surgery—intubation, treatment of fractions, sprains—and may also be employed in a shock treatment as muscle relaxants.

The compounds of the formula I as hereinbefore defined and the acid-addition salts and quaternary salts thereof—the latter being encompassed by the formula I(a)—may be prepared by the following process, which process constitutes a further feature of the present invention:

A known compound of the formula II, wherein $R_4$ is as hereinbefore defined, is reacted with an alkyl-, aryl- or aralkylsulphonic acid halide to prepare a compound of the formula III, in which $R_3$ is as hereinbefore defined; the compound of the formula III obtained is then reacted with a heterocyclic amine derivative of the formula IV

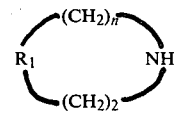

IV wherein $R_1$ and n are as hereinbefore defined; then the compound of the formula V which is obtained, $R_1$, n and the symbol ∾ are as hereinbefore defined, is reduced to give a compound of the formula VI, which is methylated to yield a compound of the formula I, wherein $R_1$, n and the symbol are as defined above, which is optionally converted into an acid addition salt thereof, or is optionally reacted with an alkyl or alkenyl halide to produce a corresponding quaternary salt of the formula I(a), wherein $R_1$, $R_2$, A, n and the symbol ∿ are as hereinbefore defined.

According to a preferred embodiment of the process of the invention the compounds of the formula I are prepared as follows:

A known compound of the general formula II [Tetrahedron 21 (4), 743–57 (1965); Helv. Chim. Acta 38, 1404 (1955)] is reacted with a sulphonic acid halide, preferably with methanesulphonic acid chloride or p-toluenesulphonic acid chloride, in a tertiary amine or in a mixture of a tertiary amine, such as pyridine and a reaction-inert solvent, preferably methylene chloride, at a temperature of below 30° C., preferably at 5° to 10° C. When the reaction terminates, the mixture is poured onto water, the precipitated product is filtered off, is released from the tertiary amine by washing with a dilute acid and subsequently with water, or alternatively the product is extracted with methylene chloride to eliminate the tertiary amine. To an alkyl- or aralkylsulphonic acid derivative of formula III obtained, a five- or six-membered heterocyclic amine containing one or two nitrogen atoms, preferably pyrrolidine, N-methylpiperazine or piperidine is added, and the mixture obtained is kept at a temperature below 140° C., preferably at the boiling point of the mixture, optionally in the presence of a solvent until the reaction terminates. Thereafter the excess of the heterocyclic amine and optionally the reaction-inert solvent are distilled off, the residue is triturated with water, filtered, and washed with water to eliminate the heterocyclic amine reactant; or alternatively the residue is evaporated, triturated with a suitable solvent, preferably with acetone or acetonitrile and is filtered off. If desired, the product obtained is purified by recrystallization or boiling. The compound of the formula V prepared in this way is reduced with a complex metal hydride, preferably with lithium-aluminum hydride or sodium-bis-(2-methoxyethoxy)-lithium-aluminum-hydride, in a reaction-inert solvent, e.g. tetrahydrofurane or dioxane, preferably at the boiling point of the reaction mixture. The reaction terminates in 1–2 to 40–50 hours. Thereafter the excess of the reducing agent is decomposed in a manner known per se, for example with water or ethyl acetate in the presence of nitrogen, the precipitate is filtered off and is washed several times preferably with the solvent used as a reaction medium. Upon evaporation of the solvent and the wash liquor the residue is crystallized.

The compound of the formula VI obtained is methylated as follows:

The compound is dissolved in an excess amount of formic acid and formeldehyde and the reaction mixture is boiled for several hours. When the reaction terminates the mixture is evaporated until a syrupy residue is obtained, which is alkalized, diluted with water, filtered and washed to neutral with water. The compound of formula I obtained is purified by crystallization from a polar solvent, for instance ether or acetone.

If desired, compounds of formula I are converted into the non-toxic physiologically compatible organic or inorganic acid-addition salts thereof, by methods known per se. In the living organism especially the inorganic hydrogen halide acid addition salts and the organic acetates, gluconates, tartarates and alkylsulphonates show the most advantageous properties.

Compounds of the formula I(a) are prepared from the bases of the formula I by dissolving a corresponding compound of formula I in a reaction-inert solvent, preferably acetone or in a mixture of acetone and methylene chloride and a solution of an excess amount of a corresponding alkyl or alkenyl halide, preferably methyl bromide, methyl iodide or allyl bromide in an appropriate solvent used as a reaction medium is added. The reaction is performed at room temperature or at the boiling temperature of the reaction mixture, under atmospheric pressure or in a bomb tube, under an overpressure of several atm. When the reaction terminates the precipitated product is filtered off, and the product is isolated optionally after distilling off the solvent or solvent mixture and the excess of the quaternarizing compound, preferably by treating with ether or acetone. The above solvent may also be added directly to the reaction mixture when the precipitated product is filtered off and, if desired, is recrystallized.

The process according to the invention is further illustrated by the following non-limiting Examples.

EXAMPLE 1

3α-Pyrrolidino-17a-methyl-17a-aza-D-homo-5α-androstane dimethobromide 2 g. (0.0055 moles) of 3α-pyrrolidino-17a-methyl-17a-aza-D-homo-5α-androstane are dissolved in a mixture of 50 ml. of dry acetone and 50 ml. of dry methylene chloride, whereupon a solution of 3.29 g. (0.034 moles) of methylbromide in 35 ml. of acetone is added to the solution. The reaction mixture is allowed to stand at room temperature for 32 hours. The progress of the reaction is monitored by thin-layer chromatography. When the reaction terminates the solvent is distilled off and the precipitated crystalline product is filtered, washed thoroughly with a 1:1 mixture of methylene chloride and acetone and is crystallized from a mixture of ethanol and ether.

Yield: 2.49 g. (81.4%) of 3α-pyrrolidino-17a-methyl-17a-aza-D-homo-5α-androstane dimethobromide M.p.: 288° to 290° C. (decomposition)
$[\alpha]_D^{25} = +28.6°$ (c: 1% in chloroform)
NMR spectrum: 0.79 (19 $CH_3$); 1.49 (18 $CH_3$); 3.11 (3 $NCH_3$); 2.94 (17a $NCH_3$).

Analysis for $C_{26}H_{48}N_2Br_2$: Calculated: C=56.93%, H=8.75%, N=5.10%, Br=29.19%; Found: C=56.71%, H=8.60%, N=5.00%, Br=28.92%.

3α-pyrrolidino-17a-methyl-17a-aza-D-homo-5α-androstane used as a starting compound is prepared as described hereinbefore.

EXAMPLE 1a

3β-Mesyloxy-17-oxo-17a-aza-D-homo-5α-androstane 40 g. (0.131 moles) of 3β-hydroxy-17-oxo-17a-aza-D-homo-5α-androstane are dissolved in 600 ml. of dry pyridine then 20.8 g. (0.181 moles) of methanesulphonic acid chloride are added to the solution with vigorous stirring so that the temperature remains between 0° and 5° C. The resultant reaction mixture is stirred for an additional 3 hours at the same temperature while the progress of the reaction is monitored by thin-layer chromatography. When the reaction terminates, the pyridine solution is added dropwise to 4000 ml. of ice-water, the precipitated product is filtered off and washed, until remove pyridine and neutralized with water, a 2% aqueous hydrochloric acid solution and again with water. The product obtained is dried at 60° C. in vacuo.

Yield: 48 g. (95.5%) of 3β-mesyloxy-17-oxo-17a-aza-D-homo-5α-androstane

M.p.: 167° to 168° C. $[\alpha]_D^{25} = +13.9°$ (c=1% in chloroform)

IR spectrum: 1170 cm$^{-1}$ ($\nu$SO$_2$); 1160 cm$^{-1}$ (amide I)

NMR spectrum: 0.82 (19 CH$_3$); 1.15 (18 CH$_3$); 3.00 (3 SO$_2$CH$_3$), 4.60 (3α H); 6.70 (17a NH).

Analysis for C$_{20}$H$_{33}$O$_4$NS: Calculated: C=62.66%, H=8.61%, N=3.65%; Found: C=62.40%, H=8.40%, N=3.50%.

EXAMPLE 1b

3β-Tosyloxy-17-oxo-17a-aza-D-homo-5α-androstane 130 g. (0.283 moles) of 3β-hydroxy-17-oxo-17a-aza-D-homo-5α-androstane are dissolved in 3900 ml. of dry pyridine, then 283 g. (1.44 moles) of freshly recrystallized p-toluene-sulphochloride are added to the solution. The reaction mixture is allowed to stand at room temperature for 24 hours, while the progress of the reaction is monitored by thin-layer chromatography. When the reaction terminates the pyridine solution is added into 20 lit. of ice water with vigorous stirring. The precipitated product is filtered off and washed, until remove pyridine and neutralized with a 2% aqueous hydrochloric acid solution and water. The product obtained is dried at 60° to 70° C. in vacuo, then boiled in 700 ml. of acetone under stirring.

Yield: 158 g. (80.7%) of 3β-tosyloxy-17-oxo-17a-aza-D-homo-5α-androstane

M.p.: 258° to 260° C. $[\alpha]_D^{25} = -2.2°$ (c=1% in chloroform)

IR spectrum: 1175 cm$^{-1}$ ($\nu$SO$_2$); 1665 cm$^{-1}$ (amide I)

NMR spectrum: 0.75 (19 CH$_3$); 1.12 (18 CH$_3$); 2.43 (tosylmethyl); 4.40 (3α H); 6.95 (17a NH).

Analysis for C$_{26}$H$_{37}$O$_4$NS: Calculated: C=67.97%, H=8.06%, N=3.05%, Found: C=67.62%, H=7.82%, N=2.90%.

EXAMPLE 1c

3α-Pyrrolidino-17-oxo-17a-aza-D-homo-5α-androstane 16 g. (0.041 moles) of 3α-mesyloxy-17-oxo-17a-aza-D-homo-5α-androstane are dissolved in 100 ml. of pyrrolidine. The solution is refluxed for 20 hours and subsequently cooled to room temperature. The precipitated crystalline substance is filtered off and washed, until remove pyrrolidine with water. The mother liquor is evaporated, the residue is triturated with water, filtered and thoroughly washed with water. The two crystalline products are combined, dried at 60° to 70° C. in vacuo, and boiled in 60 ml. of acetonitrile with stirring.

Yield: 13.7 g. (91.6%) of 3α-pyrrolidino-17-oxo-17a-aza-D-homo-5α-androstane

M.p.: 285° to 288° C. $[\alpha] = +13.3°$ (c=1% in chloroform)

IR spectrum: 1660 (amide I); 2880 to 2500 (N—CH$_2$)

Analysis for C$_{23}$H$_{38}$ON$_2$: Calculated: C=77.09%, H=10.61%, N=7.83%; Found: C=76.80%, H=10.50%, N=7.70%.

EXAMPLE 1d

3α-Pyrrolidino-17a-aza-D-homo-5α-androstane 10.5 g. (0.029 moles) of 3α-pyrrolidino-17-oxo-17a-aza-D-homo-5α-androstane are dissolved in 205 ml. of dry dioxane, whereupon 10.5 g. of lithium-aluminum hydride are carefully added to the solution under a nitrogen flow. The reaction mixture is brought to a boil in an apparatus equipped with a CaCl$_2$-tube and a reflux condenser and is refluxed for about 30 minutes. Thereafter the reaction mixture is cooled to 10° C. and the excess of lithium-aluminum hydride is decomposed with 20 ml. of water with stirring, under a vivid nitrogen flow. The precipitate consisting of lithium hydroxide and aluminum hydroxide is filtered and thoroughly washed with several portions of dioxane. The dioxane solution obtained is evaporated to dryness and the residue is purified by precipitation.

Yield: 9.1 g. (90.2%) of 3α-pyrrolidino-17a-aza-D-homo-5α-androstane

M.p.: 84° to 85° C. $[\alpha]_D^{25} = +4.6°$ (c=1% in chloroform)

NMR spectrum: 0.79 (19 CH$_3$); 1.02 (18 CH$_3$); 2.8 (17 CH$_2$)

Analysis for C$_{23}$H$_{40}$N$_2$: Calculated: C=80.23%, H=11.62%, N=8.13%; Found: C=80.01%, H=11.50%, N=7.92%.

EXAMPLE 1e

3α-Pyrrolidino-17a-methyl-17a-aza-D-homo-5α-androstane 7.1 g. (0.02 moles) of 3α-pyrrolidino-17a-aza-D-homo-5α-androstane are dissolved in a mixture of 85 ml. of formic acid and 64 ml. of formaldehyde, then the mixture is refluxed for 2.5 hours. A further 64 ml. portion of formaldehyde is added to the reaction mixture and it is refluxed for an additional 2 hours. The reaction mixture is then evaporated to near dryness and its pH-value is adjusted to 10 with a 5% aqueous sodium hydroxide solution. The precipitated amorphous substance is filtered off, washed until neutral with water, and dried at 50° to 60° C. in vacuo. The product is purified by boiling with 40 ml. of ether.

Yield: 5.6 g. (75.9%) of 3α-Pyrrolidino-17a-methyl-17a-aza-D-homo-5α-androstane

M.p.: 156° to 158° C. $[\alpha]_D^{25} = +9.8°$ (c=1% of chloroform)

NMR spectrum: 0.77 (19 CH$_3$); 0.83 (18 CH$_3$); 2.21 (17a NCH$_3$)

Analysis for C$_{24}$H$_{24}$N$_2$: Calculated: C=80.44%, H=11.73%, N=7.82%; Found: C=80.20%, H=11.52%, N=7.71%.

EXAMPLE 2

3α-Pyrrolidino-17a-methyl-17a-aza-D-homo-5α-androstane dimethoiodide 2 g. (0.0055) moles of 3α-pyrrolidino-17a-methyl-17a-aza-D-homo-5α-androstane are dissolved in a mixture of 10 ml. of acetone and 15 ml. of ethanol at the boiling temperature, then 4 g. (0.028 moles) of methyl iodide are added to the boiling reaction mixture. Boiling is continued for about 60 minutes, whereupon the reaction mixture is cooled to below 10° C., the precipitated crystals are filtered off and washed with an acetone/ethanol mixture which has the above composition.

Yield: 2.8 g. 79.09% 3α-pyrrolidino-17a-methyl-17a-aza-D-homo-5α-androstane dimethoiodide M.p.: 293° to 295° C. (decomposition) $[\alpha]_D^{25} = 28.4°$ (c=1% of an aqueous solution)

NMR spectrum: 0.80 (19 CH$_3$); 1.48 (18 CH$_3$); 2.94 (17a CH$_3$); 3.12 (3αNCH$_3$)

Analysis for C$_{26}$H$_{48}$N$_2$I$_2$: Calculated: C=49.21%, H=7.57%, N=4.41%; Found: C=49.00%, H=7.60%, N=4.30%.

EXAMPLE 3

3α-(4-Methyl-piperazino)-17a-methyl-17a-aza-D-homo-5α-androstane diallylbromide 0.3 g. (0.0007 moles) of 3α-(4-methyl-piperazino)-methyl-17a-aza-D-homo-5α-androstane are dissolved in a mixture of 5 ml. of acetone and 2 ml. of methylene chloride, then 1.39 g. 0.0114 moles of allyl bromide are added to the solution. The reaction mixture is boiled for one hour, whereupon it is cooled to room temperature and diluted with 50 ml. of ether. The precipitated solid is filtered off and crystallized from a 1:5 mixture at ethanol and ether.

Yield: 0.40 g. (82.13%) of 3α-(4-methyl-piperazino)-17a-methyl-17a-aza-D-homo-5α-androstane diallylbromide M.p.: 200° to 202° C. (decomposition) $[\alpha]_D^{25}=+3.6°$ (c=1% aqueous solution)

Analysis for $C_{31}H_{55}N_3Br_2$: Calculated: C=59.14%, H=8.74%, N=6.67%, Br=25.43%; Found: C=58.91%, H=8.50%, N=6.41%, Br=25.1%.

EXAMPLE 4

3β-Pyrrolidino-17a-methyl-17a-aza-D-homo-5α-androstane dimethobromide

The named compound is prepared starting from 3β-pyrrolidino-17a-methyl-17a-aza-D-homo-5α-androstane and methyl bromide, following the procedure described in Example 1.

Yield: 87% of 3β-pyrrolidino-17a-methyl-17a-aza-D-homo-5α-androstane dimethobromide M.p.: 270° to 280° C. (decomposition) $[\alpha]_D^{25}=0°$ (c=1% in water)

NMR spectrum: 0.81 (19 CH$_3$); 1.48 (18 CH$_3$); 2.89; 2.95 (17a NCH$_3$); 3.11 (3βNCH$_3$)

Analysis for $C_{26}H_{48}N_2Br_2$: Calculated: C=56.93%, H=8.75%, N=5.10% Br=29.19%; Found: C=56.68%, H=8.50%, N=4.90%, Br=29.00%.

3α-Mesyloxy-17-oxo-17a-aza-D-homo-5α-androstane

The named compound is prepared starting from 3α-hydroxy-17-oxo-17a-aza-D-homo-5α-androstane and methanesulphonic acid chloride, following the procedure described in Example 1a.

Yield: 87% of 3α-mesyloxy-17-oxo-17a-aza-D-homo-5α-androstane

M.p.: 174° to 176° C. $[\alpha]_D^{25}=+0.76°$ (c=1% in chloroform)

Analysis for $C_{20}H_{33}O_4NS$: Calculated: C=62.66%, H=8.61%, N=3.65%; Found: C=62.40%, H=8.50%, N=3.45%.

3β-Pyrrolidino-17-oxo-17a-aza-D-homo-5α-androstane

The named compound is prepared starting from 3α-Mesyloxy-17-oxo-17a-aza-D-homo-5α-androstane and pyrrolidine, following the procedure described in Example 1c.

Yield: 90% of 3β-pyrrolidino-17-oxo-17a-aza-D-homo-5α-androstane

M.p.: 298° to 300° C. $[\alpha]_D^{25}=+14.2°$ (c=1% in chloroform)

Analysis for $C_{23}H_{38}N_2$: Calculated: C=77.09%, H=10.61%, N=7.83%; Found: C=77.00%, H=10.40%, N=7.60%.

3β-Pyrrolidino-17a-aza-D-homo-5α-androstane

The named compound is prepared by reducing 3β-pyrrolidino-17-oxo-17a-aza-D-homo-5α-androstane with lithium-aluminum hydride, following the procedure described in Example 1d.

Yield: 87% of 3β-pyrrolidino-17a-aza-D-homo-5α-androstane

M.p.: 208° to 210° C. $[\alpha]_D^{25}=0.0°$ (c=1% in chloroform)

Analysis for $C_{23}H_{40}N_2$: Calculated: C=80.23%, H=11.62%, N=8.13%; Found: C=79.92%, H=11.40%, N=8.00%.

3β-Pyrrolidino-17a-methyl-17a-aza-D-homo-5α-androstane

The named compound is prepared starting from a mixture of 3β-pyrrolidino-17a-aza-D-homo-5α-androstane, formic acid and formaldehyde, following the procedure described in Example 1e.

Yield: 78% of 3β-pyrrolidino-17a-methyl-17-a-aza-D-homo-5α-androstane

M.p.: 148° to 150° C. $[\alpha]_D^{25}=+13.5°$ (c=1% in chloroform)

NMR spectrum: 0.75 (19 CH$_3$); 0.81 (18 CH$_3$); 2.20 (17a-NCH$_3$)

Analysis for $C_{24}H_{42}N_2$: Calculated: C=80.44%, H=11.50%, N=7.60%; Found: C=80.19%, H=11.31%, N=7.36%.

EXAMPLE 5

3β-Pyrrolidino-17a-methyl-17a-aza-D-homo-5α-androstane dimethoiodide

The named compound is prepared starting from 3β-pyrrolidino-17a-methyl-17a-aza-D-homo-5α-androstane and methyl iodide, following the procedure described in Example 2.

Yield: 88% of the 3β-pyrrolidino-17a-methyl-17a-aza-D-homo-5α-androstane dimethoiodide M.p.: 306° to 310° C. (decomposition) $[\alpha]_D^{25}=0°$ (c=1% in water)

NMR spectrum: 0.81 (19 CH$_3$); 1.48 (18 CH$_3$); 2.88; 2.93 (17a-NCH$_3$) 3.10 (3β-NCH$_3$)

Analysis for $C_{26}H_{48}N_2I_2$: Calculated: C=49.21%, H=7.57%, N=4.41%; Found: C=49.10%, H=7.31%, N=4.19%.

EXAMPLE 6

3α-(4-Dimethyl-piperazino)-17a-dimethyl-17a-aza-D-homo-5α-androstane dibromide 2 g. (0.005 moles) of 3α-(4-methyl-piperazino)-17a-methyl-17a-aza-D-homo-5α-androstane are dissolved in a mixture of 25 ml. of acetone and 25 ml. of methylene chloride, then a solution of 2.85 g. (0.03 moles) of methyl bromide in 19 ml. of acetone is added. The reaction mixture is allowed to stand at room temperature for 24 hours, whereupon the precipitated crystals are filtered off and washed thoroughly with a 1:1 mixture of acetone and methylene chloride.

The product is dissolved in ethanol and the quaternary product is precipitated upon addition of ether.

Yield: 2.6 g. (87.2%) of 3α-(4-dimethyl-piperazino)-17a-dimethyl-17a-aza-D-homo-5α-androstane dibromide M.p.: 284° to 286° C. (decomposition) $[\alpha]_D^{25}=+2.2°$ (c=1% in water)

NMR spectrum: 0.78 (19 CH$_3$); 1.45 (18 CH$_3$); 2.93 (17a-NCH$_3$); 3.10; 3.15 (3α4-dimethyl-piperazine)

Analysis for $C_{27}H_{51}N_3Br_2$: Calculated: C=56.15%, H=8.83%, N=7.27%, Br=27.27%; Found: C=56.00%, H=8.60%, N=7.02%, Br=27.50%.

3α-(4-Methyl-piperazino)-17a-methyl-17a-aza-D-homo-5α-androstane used as a starting compound is prepared as follows:

3α-(4-methyl-piperazino)-17-oxo-17a-aza-D-homo-5α-androstane 12 g. (0.031 moles) of 3β-mesyloxy-17-oxo-17a-aza-D-homo-5α-androstane are dissolved in 72 ml. of N-methylpiperazine. The solution obtained is refluxed for 22 hours then is cooled to room temperature. The precipitated crystalline product is filtered off, washed, until N-methylpiperazine-free, with water at 5° C. and thereafter is dried at a temperature of 60° to 70° C. until it reaches a steady weight.

The crystalline product is purified by boiling in acetonitrile.

Yield: 10.2 g. (84.1%) of 3α-(4-methyl-piperazino)-17-oxo-17a-aza-D-homo-5α-androstane M.p.: 268° to 270° C. $[\alpha]_D^{25} = +11.3°$ (c=1% in chloroform)

IR spectrum: 1680 cm$^{-1}$ amide I

NMR spectrum: 0.80 (19 CH$_3$); 1.13 (18 CH$_3$); 2.27 (4-methyl-piperazine)

Analysis for $C_{24}H_{41}ON_3$: Calculated: C=74.41%, H=10.59%, N=10.85%; Found: C=74.20%, H=10.36%, N=10.61%.

3α-(4-methyl-piperazino)-17a-aza-D-homo-5α-androstane 7 g. (0.018 moles) of 3α-N-methylpiperazino-17-oxo-17a-aza-D-homo-5α-androstane are dissolved in 140 ml. of dry dioxane, then 7 g. of lithium-aluminum hydride are added to the solution, under a nitrogen flow and vigorous stirring. The reaction mixture is boiled in a flask equipped with a reflux condenser supplied with a CaCl$_2$-tube, under a nitrogen flow for 32 hours. The reaction mixture is then cooled to 10° C., whereupon the excess of lithium-aluminum hydride is decomposed with 15 ml. of water, under vigorous stirring and intensive nitrogen flow.

The precipitate, which consists of lithium hydroxide and aluminum hydroxide is filtered off and washed several times with dioxane. The dioxane solution is evaporated to dryness and the residue is crystallized from acetonitrile.

Yield: 6.0 g. (89.0%) of 3α-(4-methyl-piperazino)-17a-aza-D-homo-5α-androstane

M.p.: 119° to 120° C. $[\alpha]_D^{25} = +2.6°$ (c=1% in chloroform)

NMR spectrum: 0.80 (19 CH$_3$); 1.03 (18 CH$_3$); 2.27 (4-methyl-piperazine); 2.80 (17-CH$_2$).

Analysis for $C_{24}H_{43}N_3$: Calculated: C=77.21%, H=11.52%, N=11.26%; Found: C=77.00%, H=11.31%, N=11.02%.

3α-(4-methyl-piperazino)-17a-methyl-17a-aza-D-homo-5α-androstane 4.1 g. (0.010 moles) of 3α-N-methyl-piperazino-17a-aza-D-homo-5α-androstane are dissolved in a mixture of 48 ml. of formic acid and 37 ml. of formaldehyde and the reaction mixture is refluxed for 2.5 hours. Thereafter a further 37 ml. portion of formaldehyde is added to the reaction mixture and boiling is continued for an additional two hours. The reaction mixture is then evaporated to nearly dryness and the pH-value is adjusted to 10 with a 5% aqueous sodium hydroxide solution. The precipitated amorphous product is filtered off, washed to neutral with water and dried at a temperature of 50° to 60° C. in vacuo. The product is crystallized from ether.

Yield: 3.3 g. (77.64%) of 3α-(4-methyl-piperazino)-17a-methyl-17a-aza-D-homo-5α-androstane M.p.: 152° to 155° C. $[\alpha]_D^{25} = +16.5°$ (c=1% in chloroform)

NMR spectrum: 0.77 (19 CH$_3$); 0.82 (18 CH$_3$); 2.18 (17a-NCH$_3$); 2.26 (4-methylpiperazine)

Analysis for $C_{25}H_{45}N_3$: Calculated: C=77.51%, H=11.62%, N=10.85%; Found: C=77.30%, H=11.40%, N=10.60%.

EXAMPLE 7

3α-Piperidino-17a-methyl-17a-aza-D-homo-5α-androstane dimethoiodide

The named compound is prepared starting from 3α-piperidino-17a-methyl-17a-aza-D-homo-5α-androstane and methyl iodide, following the procedure described in Example 2.

Yield: 85% of 3α-piperidino-17a-methyl-17a-aza-D-homo-5α-androstane dimethoiodide M.p.: 274° to 276° C. $[\alpha]_D^{25} = +32.2°$ (C=1% in water)

Analysis for $C_{27}H_{50}N_2I_2$: Calculated: C=49.39%, H=7.62%, N=4.26%, I=38.70%; Found: C=49.10%, H=7.41%, N=4.00%, I=38.40%.

3αPiperidino-17-oxo-17a-aza-D-homo-5α-androstane

The named compound is prepared starting from 3β-mesyl-oxy-17-oxo-17a-aza-D-homo-5α-androstane and piperidine, following the procedure described in Example 1c.

Yield: 90% of 3α-piperidino-17-oxo-17a-aza-D-homo-5α-androstane

M.p.: 270° to 272° C. $[\alpha]_D^{25} = +13.7°$ (c=1% in chloroform)

IR spectrum: 1675 cm$^{-1}$ amide I

Analysis for $C_{24}H_{40}N_2O$: Calculated: C=77.41%, H=10.75%, N=7.52%; Found: C=77.19%, H=10.50%, N=7.31%.

3α-Piperidino-17a-aza-D-homo-5α-androstane

The named compound is obtained starting from 3α-piperidino-17-oxo-17a-aza-D-homo-5α-androstane by reduction with lithium-aluminum hydride, following the procedure described in Example 1d.

Yield: 81% of 3α-piperidino-17a-aza-D-homo-5α-androstane

M.p.: 108° to 110° C. $[\alpha]_D^{25} = +7.6°$ (c=1% in chloroform)

Analysis for $C_{24}H_{42}N_2$: Calculated: C=78.21%, H=11.73%, N=7.60%; Found: C=78.03%, H=11.54%, N=7.79%

3α-Piperidino-17a-methyl-17a-aza-D-homo-5α-androstane

The title compound is prepared starting from 3α-piperidino-17a-aza-D-homo-5α-androstane by alkylation with a mixture of formic acid and formaldehyde, following the procedure described in Example 1e.

Yield: 85% of 3α-piperidino-17a-methyl-17a-aza-D-homo-5α-androstane

M.p.: 176° to 177° C. $[\alpha]_D^{25} = +17.8°$ (c=1% in chloroform)

Analysis for $C_{25}H_{44}N_2$: Calculated: C=80.64%, H=11.82%, N=7.52%; Found: C=80.73%, H=11.58%, N=7.72%

EXAMPLE 8

3α-Pyrrolidino-17a-methyl-17a-aza-D-homo-5α-androstane diethanesulphonate 2 g. of 3α-pyrrolidino-17a-methyl-17a-aza-D-homo-5α-androstane are dissolved in 30 ml. of dry ethanol, then 1.2 g. of ethanesulphonic acid are added to the solution. Thereafter ⅔ of the ethanol is distilled off, then 50 ml. of ether are added to the residue. The precipitated white crystalline substance is filtered off, thoroughly washed with several portions of ether and is dried over phosphorous pentoxide in vacuo.

Yield: 3.0 g. (93.7%) of 3α-pyrrolidino-17a-methyl-17a-aza-D-homo-5α-androstane diethanesulphonate M.p.: 268° to 270° C. (decomposition) $[\alpha]_D^{25} = +62°$ (c=1% in water)

Analysis for $C_{28}H_{54}S_2N_2O_6 \cdot H_2O$: Calculated: C=58.13%, H=9.34%, N=4.84%; Found: C=57.92%, H=9.10%, N=4.62%.

EXAMPLE 9

Injection solution 10 g. of 3α-pyrrolidino-17a-methyl-17a-azo-D-homo-5α-androstane dimethobromide are dissolved in 2000 ml. of pyrogene-free physiological sodium chloride solution and thereafter the solution obtained is filled into ampules. Into a 2-ml. brown ampule 1 ml. of the above injection solution is filled. The ampules are sterilized in a known manner.

What we claim is:

1. A 3-amino-17a-aza-D-homoandrostane compound of the formula I

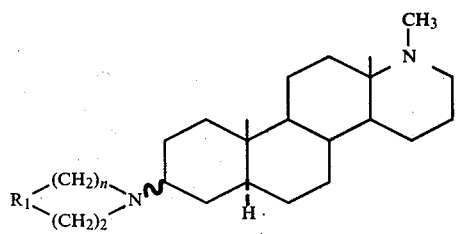

wherein
$R_1$ is methylene or an >N—CH₃ group;
n is 1 or 2; and
the symbol ⌒ represents an α- or β-configuration; or an acid-addition salt or quaternary salt of the formula I(a)

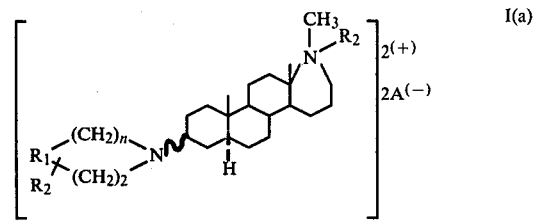

thereof, wherein
$R_2$ is $C_1$ to $C_4$ alkyl or $C_1$ to $C_4$ alkenyl; and
A is halogen;
but where $R_1$ is >N—CH₃,
$R_2$ is attached to the nitrogen of the >N—CH₃ group.

2. A quaternary salt of the formula I(a)

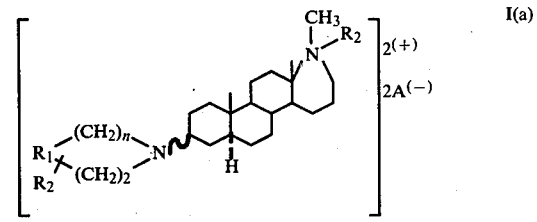

wherein
$R_1$ is methylene or >N—CH₃;
$R_2$ is $C_1$ to $C_4$ alkyl or $C_1$ to $C_4$ alkenyl
a is halogen;
n=1 or 2;
but where $R_1$ is N—CH₃,
$R_2$ is attached to the nitrogen of said N—CH₃.

3. A compound as defined claim 1 which is 3α-pyrrolidino-17a-methyl-17a-aza-D-homo-5α-androstane dimethoiodide.

4. A compound as defined in claim 1 which is 3β-pyrrolidino-17a-methyl-17a-aza-D-homo-5α-androstane dimethoiodide.

5. A compound as defined in claim 1 which is 3α-pyrrolidino-17a-methyl-17a-aza-D-homo-5α-androstane dimethobromide.

6. A compound as defined in claim 1 which is 3β-pyrrolidino-17a-methyl-17a-aza-D-homo-5α-androstane dimethobromide.

7. A muscle relaxant composition which comprises at least one acid-addition or quaternary salt of the formula I(a) as defined in claim 1 in association with a pharmaceutically acceptable carrier.

* * * * *